(12) United States Patent
Cao et al.

(10) Patent No.: US 11,630,107 B2
(45) Date of Patent: Apr. 18, 2023

(54) METHOD AND SYSTEM FOR DETECTING TARGET COMPONENTS BY UTILIZING MOBILE TERMINAL

(71) Applicant: Institute of Quality Standard and Testing Technology for Agro-Products, CAAS, Beijing (CN)

(72) Inventors: Zhen Cao, Beijing (CN); Jing Wang, Beijing (CN)

(73) Assignee: Institute of Quality Standard and Testing Technology for Agro-Products, CAAS, Beijing (CN)

(*) Notice: Subject to any disclaimer, the term of this patent is extended or adjusted under 35 U.S.C. 154(b) by 0 days.

(21) Appl. No.: 17/744,556

(22) Filed: May 13, 2022

(65) Prior Publication Data
US 2022/0283155 A1 Sep. 8, 2022

Related U.S. Application Data

(63) Continuation of application No. PCT/CN2020/127664, filed on Nov. 10, 2020.

(30) Foreign Application Priority Data

Nov. 15, 2019 (CN) .......................... 201911126008.1

(51) Int. Cl.
*G01N 33/543* (2006.01)
*G06T 7/11* (2017.01)
(Continued)

(52) U.S. Cl.
CPC ...... *G01N 33/54388* (2021.08); *B01L 3/5023* (2013.01); *G01N 21/78* (2013.01);
(Continued)

(58) Field of Classification Search
CPC ............. G01N 33/54388; G01N 21/78; G01N 2021/7759; G01N 2201/0221;
(Continued)

(56) References Cited

U.S. PATENT DOCUMENTS

| 2005/0208593 | A1  | 9/2005 | Vail et al. |
| 2010/0120173 | A1* | 5/2010 | Zhou ..................... B01L 3/5025 422/400 |

(Continued)

FOREIGN PATENT DOCUMENTS

| CN | 1922488  | 2/2007 |
| CN | 101261270 | 9/2008 |

(Continued)

*Primary Examiner* — Dennis White
(74) *Attorney, Agent, or Firm* — Morrison & Foerster LLP

(57) ABSTRACT

A method and system for detecting a target component by using a mobile terminal, and a detection method for simultaneously screening multiple target objects. The method for detecting a target component by using a mobile terminal comprises: detecting a target component by using test strips (100) to obtain chromogenic test strips (100); arranging the test strips (100) around a same circle center at equal angles to obtain an arrangement ring of test strips (100), positioning identifiers being provided on an area outside the test strips (100) on the arrangement ring of the test strips (100); performing image acquisition on the arrangement ring of the test strips (100) by using a mobile terminal, and uploading an acquired image to a data processing center, correcting the acquired image according to the positioning identifiers; determining the positions of a personalized mark area and a result display area of each test strip (100) in the image; performing segmentation to obtain images of the personalized mark area and the result display area of each test strip (100); calculating a chromogenic result of the result display area, and obtaining a test result of the target component; and (Continued)

outputting the test result of the target component and displaying the test result on the mobile terminal.

28 Claims, 5 Drawing Sheets

(51) Int. Cl.

| | | |
|---|---|---|
| *G06T 7/73* | (2017.01) | |
| *G06T 7/13* | (2017.01) | |
| *G06T 7/90* | (2017.01) | |
| *B01L 3/00* | (2006.01) | |
| *G01N 21/78* | (2006.01) | |
| *G01N 21/77* | (2006.01) | |

(52) U.S. Cl.
CPC ............... *G06T 7/11* (2017.01); *G06T 7/13* (2017.01); *G06T 7/73* (2017.01); *G06T 7/90* (2017.01); *B01L 2300/021* (2013.01); *B01L 2300/069* (2013.01); *G01N 2021/7759* (2013.01); *G06T 2207/30204* (2013.01)

(58) Field of Classification Search
CPC .......... G01N 21/8483; G01N 33/5302; G01N 33/558; B01L 3/5023; B01L 2300/021; B01L 2300/069; B01L 9/52; B01L 2300/0825; G06T 7/11; G06T 7/13; G06T 7/73; G06T 7/90; G06T 2207/30204; G06T 5/006; G06T 2207/10024; G06T 7/0012

See application file for complete search history.

(56) References Cited

U.S. PATENT DOCUMENTS

| | | | |
|---|---|---|---|
| 2013/0302830 A1 | 11/2013 | Mehra et al. | |
| 2015/0211987 A1* | 7/2015 | Burg | ................ G01N 21/78 |
| | | | 356/402 |
| 2018/0264464 A1* | 9/2018 | Greef | ................ B01L 3/5023 |

FOREIGN PATENT DOCUMENTS

| | | | |
|---|---|---|---|
| CN | 203606293 | | 5/2014 |
| CN | 104964973 | | 10/2015 |
| CN | 204789347 | | 11/2015 |
| CN | 105378460 | | 3/2016 |
| CN | 105388147 | | 3/2016 |
| CN | 105659071 | | 6/2016 |
| CN | 205538992 | | 8/2016 |
| CN | 106056156 | | 10/2016 |
| CN | 206515242 | | 9/2017 |
| CN | 206515242 U | * | 9/2017 |
| CN | 109870448 | | 6/2019 |
| CN | 209894828 | | 1/2020 |
| CN | 110780064 | | 2/2020 |
| WO | WO 2021/093555 | | 5/2021 |
| WO | WO 2021/093714 | | 5/2021 |

* cited by examiner

METHOD AND SYSTEM FOR DETECTING TARGET COMPONENTS BY UTILIZING MOBILE TERMINAL

CROSS-REFERENCE TO RELATED APPLICATIONS

This application is a continuing application of International Application No. PCT/CN2020/127664, filed internationally on Nov. 10, 2020, which claims the priority of the Chinese patent application No. 201911126008.1, titled "Method and System for Detecting Target Components by Utilizing Mobile Terminal", filed on Nov. 15, 2019 to China National Intellectual Property Administration, the disclosures of which are hereby incorporated by reference.

TECHNICAL FIELD

The present disclosure relates to the technical field of immunological detection, and more particularly relates to a method and system for detecting target components by utilizing a mobile terminal, and a detection method for simultaneously screening multiple targets.

BACKGROUND ART

At present, targets are generally rapidly detected by an immunochromatographic method. The immunochromatographic method is conducted in the form of a test strip. Different kinds of the test strips have different reading manners, so that use difficulty of the test strips in non-professional groups is increased; and the requirement of detecting the targets in real time cannot be met.

In addition, even if the test strips are used by professional people, test lines on the test strips may have different color depths while encountering targets of different concentrations. Interpretation of qualitative or quantitative detection of the targets performed by observing color-developing results of the test strips by naked eyes is often affected by personal subjective factors of operators, thereby causing determination inaccuracy of detection results.

In the prior art, to eliminate influences of the personal subjective factors, most of the test strips are read by a designed test strip reader. The test strip reader has a light source of specific intensity at a specific position, and is provided with a camera at a specific position. Moreover, generally in a cassette, after images are shot, a color-developing area is relatively fixed; and the data is relatively accurately read. However, the test strip reader is inconvenient to carry, high in price, and unsuitable for ordinary consumers to detect the targets at any time.

Therefore, a method that has low requirements on professional degrees of the operators and can qualitatively or quantitatively detect the targets under conventional ambient light conditions anytime anywhere needs to be provided in the art. Meanwhile, the detection results have higher reliability.

SUMMARY OF THE INVENTION

A purpose of embodiments of the present disclosure is to provide a method for detecting target components by utilizing a mobile terminal. The method can simultaneously detect multi-target components by utilizing the mobile terminal, is not influenced by factors such as types of mobile terminals and inclination of shooting angles, and has characteristics that requirements on professional degrees of operators are low and the targets can be qualitatively or quantitatively detected under conventional ambient light conditions anytime anywhere.

The embodiments of the present disclosure provide a method for detecting target components by utilizing the mobile terminal. The method includes the following steps: detecting to-be-detected sample solutions by test strips to obtain color-developed test strips, wherein the test strips at least include a personalized mark area and a result display area;

arranging the test strips in an equal angle surrounding the same center of a circle to obtain a test strip arrangement ring; and arranging location identifiers in a detection disc area outside the test strips on the test strip arrangement ring;

performing image acquisition on the test strip arrangement ring by the mobile terminal; and uploading acquired images to a data processing center;

identifying the location identifiers in the acquired images; correcting the acquired images according to the location identifiers; determining positions of the personalized mark area and the result display area in each of the test strips in the corrected images according to a preset positional relationship between the location identifiers and the test strips; and segmenting images according to the determined positions of the personalized mark area and the result display area in each of the test strips to obtain the images of the personalized mark area and the result display area in each of the test strips; calculating color-developing results of the result display areas; comparing the color-developing results with standard color-developing results in a pre-established standard database matched with identity information in the personalized mark areas; and acquiring test results of the target components; and outputting the test results of the target components; and displaying the test results on the mobile terminal.

In the above implementation process, the personalized mark area is arranged on each of the test strips; and identity information used for identifying the types of the test strips is set in the personalized mark area. The test strips are arranged in the equal angle surrounding the same center of a circle. With respect to a combination of test strips in a non-circumferential array, images of different test strips may have significant differences during shooting because everything looks small in the distance and big on the contrary. According to the circumferential arrangement manner in the present disclosure, image distortion of the acquired test strips tends to be the same. The acquired images of the test strips are corrected by the location identifiers, so that the image distortion caused by reasons such as jitter and angle inclination in the image acquisition process is eliminated. Based on the condition that the images of the test strips almost have no distortion, accurate positions of the personalized mark area and the result display area in the image of each of the test strips are obtained according to the preset positional relationship, so that a higher matching degree between the segmented result display area and an actual result display area is ensured in image processing procedures of the result display areas of the test strips; and more accurate detection results can be further obtained after the read value is compared with a matched standard numerical value. Thus it can be seen that, the method in the present disclosure has low requirements on professional degrees of the operators and can qualitatively or quantitatively detect the targets under the conventional ambient light conditions anytime anywhere. Meanwhile, the detection results have higher accuracy.

In one possible implementation, the step of correcting the acquired images according to the location identifiers includes:
correcting shooting angles; and correcting the position deviation.

In the above implementation process, by correcting the acquired images, locations, sizes and arrangement directions of objects such as the test strips and location identifiers in the acquired images may be the same as or has a set proportional relation with locations, sizes and arrangement directions of actual objects, i.e., the images and the actual objects may be the same or be scaled up or reduced in an equal proportion. When test strips of the same specification and dimension are adopted, the corrected images of the test strips basically have the same distortion; and the result display areas for image segmentation have basically consistent areas. Therefore, identification accuracy of the color-developing results of the result display areas is increased, thereby ensuring reliability of the detection results.

In one possible implementation, the step of correcting the acquired images according to the location identifiers includes: identifying positions and/or shapes of the location identifiers; and correcting shooting angles of the acquired images and/or correcting the position deviation of the acquired images according to the positions and/or shapes of the location identifiers.

The location identifiers have features (such as shape, boundary, position, size and color) that can be obviously distinguished from surroundings. By identifying the features of the location identifiers, the location identifiers are matched with features of preset identifiers in the data processing center so as to correct the images. The correction process is more accurate; and an algorithm is simpler. Compared with a method for directly identifying edges of the test strips (or the color-developing area), the method in the present disclosure is clearer in features (particularly the boundary) of the location identifiers, accurate in identification and accurate in correction result, thereby increasing the identification accuracy of the color-developing results and ensuring the reliability of the detection results.

In one possible implementation, the location identifiers have preset shapes and are arranged at preset positions.

The location identifiers have the preset shapes and the preset positions; and during image identification, the shapes and positions of the location identifiers of the acquired images can be matched by the data processing center according to the preset shapes and the preset positions, thereby correcting the acquired images.

In one possible implementation, the shapes of the location identifiers are shapes that have obvious vertexes and straight sides.

In the identification process of the location identifiers, the obvious vertexes and straight sides are easily identified, so that the identification is more accurate, and the accuracy of image correction can be increased.

In one possible implementation, the test strip arrangement ring is obtained by limiting the test strips on a detection disc; the location identifiers are tag blocks arranged on the detection disc, and/or the location identifiers are the edges of the detection disc.

The location identifiers are identifiers that can locate the test strips in the data acquisition process; and these location identifiers may be specific tag blocks, or may be certain structural features of the detection disc containing the test strips (such as the edges of the detection disc).

Optionally, the tag blocks are distinction tag blocks and contrast tag blocks. The distinction tag blocks and contrast tag blocks are used for tagging arrangement orders and positions of the test strips.

In one possible implementation, the step of segmenting the images of the personalized mark area and the result display area in each of the test strips includes:
identifying the tag blocks in the acquired images; correcting the acquired images according to the tag blocks; determining positions of the personalized mark area and the result display area in each of the test strips in the corrected images according to a preset positional relationship between the tag blocks and the test strips; and segmenting the images according to the determined positions of the personalized mark area and the result display area in each of the test strips to obtain segmented images of the personalized mark area and the result display area in each of the test strips.

In another possible implementation, the step of segmenting the images of the personalized mark area and the result display area in each of the test strips includes:
identifying edges of detection discs in the acquired images; correcting the acquired images according to the edges of detection discs; determining positions of the personalized mark area and the result display area in each of the test strips in the corrected images according to a preset positional relationship between the edges of the detection discs and the test strips; and segmenting the images according to the determined positions of the personalized mark area and the result display area in each of the test strips to obtain segmented images of the personalized mark area and the result display area in each of the test strips.

In another possible implementation, the step of segmenting the images of the personalized mark area and the result display area in each of the test strips includes:
identifying the tag blocks and the edges of the detection discs in the acquired images; correcting the acquired images according to the tag blocks and the edges of detection discs; determining positions of the personalized mark area and the result display area in each of the test strips in the corrected images according to common information of the tag blocks and the edges of detection discs and a preset positional relationship between the common information and the test strips; and segmenting the images according to the determined positions of the personalized mark area and the result display area in each of the test strips to obtain segmented images of the personalized mark area and the result display area in each of the test strips.

As mentioned above, the implementation of identifying the location identifiers in the acquired images, correcting the acquired images according to the location identifiers and segmenting the images of the personalized mark area and the result display area in each of the test strips may be understood as follows: the acquired images may be corrected by the tag blocks only, may also be corrected by the edges of the detection discs only, and may further be corrected by both the tag blocks and the edges of the detection discs. In the implementation of correcting the images by the tag blocks and the edges of the detection discs, correction results of the tag blocks and detection results of the edges of the detection discs may be mutually corrected, thereby increasing the accuracy of image correction, increasing the identification precision and the accuracy of the color-developing area and increasing the reading accuracy of the color-developing result of the color-developing area.

In one possible implementation, the result display area in each test strip includes a T line and a C line. The color-developing result is a ratio of an image chroma value of the T line to an image chroma value of the C line; or the color-developing result is an image chroma value of the T line; and the chroma value includes an RGB value, a gray value or a photometric value.

In one possible implementation, the step of calculating the color-developing result as the ratio of the image chroma value of the T line to the image chroma value of the C line includes:

taking a ratio of the image chroma value of the T line relative to a background color to the image chroma value of the C line relative to the background color as the color-developing result.

Optionally, a selection area of the background color is located nearby the T line or the C line in the result display area; and optionally, the selection area of the background color is located between the T line and the C line.

In one possible implementation, the step of detecting the target components by the test strips includes: respectively arranging the test strips in a plurality of sample containing cavities for containing the target components, wherein the volumes of sample solution in the plurality of sample containing cavities are the same; and the test strips arranged in the sample containing cavities have the same angle of inclination and the same arrangement time.

In the above implementation process, the test strips conduct chromatographic assay in the sample solutions of the same volume according to the same angle. The chromatographic behavior is consistent; differences of the color-developing results brought by operating errors can be decreased; and the reliability of the color-developing results is increased.

In one possible implementation, the method for detecting the target components by utilizing the mobile terminal further includes a step of calibrating orders of the test strips in the test strip arrangement ring by the tag blocks.

Optionally, the test strips in the test strip arrangement ring are sorted in sequence clockwise or anticlockwise by taking one tag block that can be distinguished from the rest tag blocks as a starting point of the order.

In one possible implementation, pixels of image acquisition equipment of the mobile terminal are at least 8 million.

The embodiments of the present disclosure further provide a method for the simultaneous determination of multiple targets, including:

containing to-be-detected liquid sample solutions in a plurality of sample containing cavities;

conducting the chromatographic assay on the samples in the sample containing cavities by test strips, wherein each of the test strips at least includes a personalized mark area and a result display area;

arranging the test strips on a detection disc provided with location identifiers after the chromatographic assay, wherein due to the detection disc, the test strips can be arranged in the same circular ring area in an equal angle surrounding the center of the detection disc;

performing image acquisition on the detection disc and the test strips on the detection disc by utilizing the mobile terminal;

uploading the acquired images to a data processing center for performing data processing; identifying the location identifiers in the acquired images; correcting the acquired images according to the location identifiers; determining positions of the personalized mark area and the result display area in each of the test strips according to a preset positional relationship between the location identifiers and the test strips; segmenting images according to the determined positions of the personalized mark area and the result display area in each of the test strips to obtain segmented images of the personalized mark area and the result display area in each of the test strips; and acquiring detection results of the targets; and returning the detection results of the targets to the mobile terminal.

The embodiments of the present disclosure further provide a method for the simultaneous determination of multiple targets, including:

containing to-be-detected liquid sample solutions in a plurality of sample containing cavities in the bottoms of which liquid dropping pipelines are formed;

arranging test strips on a detection disc provided with location identifiers, wherein the test strips are arranged in one circular ring area of the detection disc in an equal angle surrounding the center of the detection disc; and each of the test strips at least includes a personalized mark area, a result display area and a liquid-absorbing area;

correspondingly arranging the liquid dropping pipelines of the plurality of sample containing cavities above the liquid-absorbing area of each of the test strips, so as to conduct the chromatographic assay on liquid samples in the sample containing cavities by the test strips;

performing image acquisition on the detection disc and the test strips on the detection disc by utilizing the mobile terminal after the chromatography of the test strips is completed;

uploading the acquired images to a data processing center for performing data processing; identifying the location identifiers in the acquired images; correcting the acquired images according to the location identifiers; determining positions of the personalized mark area and the result display area in each of the test strips according to a preset positional relationship between the location identifiers and the test strips; segmenting images according to the determined positions of the personalized mark area and the result display area in each of the test strips to obtain segmented images of the personalized mark area and the result display area in each of the test strips; and acquiring detection results of the targets; and returning the detection results of the targets to the mobile terminal.

In a possible detection, the location identifiers arranged on the upper surface of the detection disc are tag blocks, used for locating and tagging the test strips in the image acquisition and processing procedures.

The tag blocks may achieve an effect of correcting the images. Meanwhile, when the images are detected by utilizing the edges of the detection disc and the detection blocks, the accuracy of image correction can be increased.

Optionally, the tag blocks include distinction tag blocks and contrast tag blocks; and the distinction tag blocks are used for being distinguished from the contrast tag blocks.

Optionally, the total number of the distinction tag blocks and contrast tag blocks is not less than three. The arrangement order of the test strips can be tagged by the distinction tag blocks and contrast tag blocks. The shooting angles can be well corrected by more than three tag blocks.

Optionally, shapes of the tag blocks at least include vertexes and straight sides.

The tag blocks including the vertexes and straight sides are easily identified and located, so that the images are accurately corrected.

Optionally, the tag blocks include one blue square color block and three green square color blocks, or the tag blocks include one green square color block and three blue square color blocks.

Blue, green and yellow are stable colors; and when the identifier edges are identified, the colors are not easily affected by the ambient light, and identification results are more accurate.

In one specific implementation, the upper surface of the detection disc is a regular polygon.

The regular polygon is provided with specific vertexes and sides. Thus, the regular polygon is easily identified during image processing and matched with a preset shape of the data processing center, i.e., the image correction is more accurate.

Optionally, the upper surface of the detection disc is a neutral color surface.

Optionally, the upper surface of the detection disc is a diffuse reflection surface.

The neutral color surface is slightly affected by an external light source, and the reflected light of the surface has little interference on the color of the color-developing area. When data is read, the color-developing result is accurately read. Light spots reflected by the light source do not occur on the diffuse reflection surface, so as not to cause interference on image acquisition.

In one possible implementation, when the chromatographic assay is conducted on the samples in the sample containing cavities by the test strips, the sample solutions in the plurality of sample containing cavities have the same quantity; and contact time of the test strips and the liquid samples in the sample containing cavities is the same.

Under the same test condition, errors of the color-developing results brought by operating errors can be decreased.

Optionally, when the test strips are inserted into the sample containing cavities, the inclination angle of the test strips inserted into the sample containing cavities is the same.

With respect to the operations of detecting the sample solutions by conducting chromatography on the test strips and arranging the test strips in the circumferential manner, the insertion angles of the test strips are variable factors of the operations; and the errors of result display brought by the operating errors can be decreased by the same insertion angle of the test strips.

Optionally, when the test strips are located at the bottoms of the sample containing cavities, the positions of the liquid dropping pipelines arranged above the-liquid-absorbing area of the test strips are the same.

When the test strips are directly arranged in the circumferential manner, the chromatographic assay of the test strips is conducted by leaking the sample solutions in the sample containing cavities. Contact positions of the sample solutions on the test strips are also variable factors of the operations. The errors of result display brought by the operating errors can also be decreased by the same contact position of the sample solutions.

In one possible implementation, after the test strips are arranged on the detection disc, the upper surface of the test strips is flush with the upper surface of the detection disc.

Optionally, the upper surface of the result display area is flush with the upper surface of the detection disc.

The upper surface of the test strip (particularly the upper surface of the result display area of the test strip) is flush with the upper surface of the detection disc, so that shadow caused by light irradiation can be decreased; the accuracy of chroma identification for the color-developing area during data processing is increased; and the accuracy of the detection result is increased.

In one possible implementation, pixels of image acquisition equipment of the mobile terminal are at least 8 million.

The higher the pixel is, the higher the identification accuracy of the location identifiers is; the higher the accuracy of image correction is; the more accurate the segmentation of the color-developing area is; the more accurate the identification of the color-developing result is, and the more reliable the detection result is.

In one possible implementation, test strip containing grooves that are recessed downwards from the upper surface of the detection disc are formed in the detection disc, and are used for containing the test strips.

The test strip containing grooves can achieve effect of limiting the test strips, thereby avoiding slide of the test strips due to problems such as placement angles.

Optionally, isolation blocks used for separating the lower surfaces of the test strips from the bottoms of the test strip containing grooves are arranged at the bottoms of the test strip containing grooves.

The test strips can be separated from the bottoms of the test strip containing grooves by the isolation block, thereby preventing the sample solutions on the test strips from contaminating the test strip containing grooves, decreasing the sample contamination during the continuous sample detection and increasing the accuracy of detection result.

Optionally, when the test strips are put into the test strip containing grooves, the personalized mark area is close to the center of a circle of the detection disc, and the border of an area containing the test strips in the test strip containing grooves is matched with the shape of the test strips.

When the border of the area containing the test strips in the test strip containing grooves is matched with the shape of the test strips, gaps between the test strips and the test strip containing grooves can be decreased, and a condition that the gaps are identified as one part of personalized marks in the personalized mark area by the data processing center so as to affect selection of the standard database is avoided. Meanwhile, interference of shadow of the gaps on identification of the T lines and C lines in the result display area can also be avoided.

The embodiments of the present disclosure further provide a system for detecting target components by utilizing a mobile terminal, including:

a sample solution detection device, including test strips and a detection disc, wherein each of the test strips at least includes a personalized mark area and a result display area; the detection disc is used for limiting the test strips to be arranged in an equal angle surrounding the same center of a circle to obtain a test strip arrangement ring; and location identifiers used for locating the test strips in the test strip arrangement ring after image acquisition are arranged on the detection disc;

an image acquisition device, arranged on the mobile terminal, and configured to perform image acquisition on the test strip arrangement ring;

a data processing device, configured to perform data processing on the acquired images, identify the location identifiers in the acquired images, correct the acquired images according to the location identifiers, determine positions of the personalized mark area and the result display area in each of the test strips in the corrected images according to a preset positional relationship between the location identifiers and the test strips, segment images according to the determined positions of the personalized mark area and the result display area in each of the test strips to obtain the images of the personalized mark area and the result display area in each of the test strips, and obtain test results of the target components; and a test result receiving device, configured to receive the test results of the target components and arranged on the mobile terminal.

According to the system for detecting the target components by utilizing the mobile terminal, the mounted devices are simple; the detection device for sample solution is small in size and easy to carry; and the image acquisition device, the data processing device and the test result receiving device may be mounted on the mobile terminal or cloud. Thus, operating difficulty is lowered; and then promotion of the detection method of the target components is more convenient. In addition, the system for detecting the target components by utilizing the mobile terminal can realize multichannel detection and has reliable detection results.

In one possible implementation, the system is used for conducting the method for detecting the target components by utilizing the mobile terminal provided by the embodiments of the present disclosure, or the system is used for conducting the method for the simultaneous determination of the multiple targets provided by the embodiments of the present disclosure.

The system for detecting the target components by utilizing the mobile terminal may perform detection in different manners, preferably is used for conducting the method for detecting the target components by utilizing the mobile terminal provided by the embodiments of the present disclosure, or conducting the method for the simultaneous determination of the multiple targets provided by the embodiments of the present disclosure.

In one possible implementation manner, the data processing device includes:

an image correction unit, configured to identify the location identifiers in the acquired images and correct the acquired images according to the location identifiers;

an image segmentation unit, configured to segment images of the personalized mark area and the result display area in each of the test strips; and a calculation unit, configured to calculate color-developing results of the result display areas, and compare the color-developing results with standard color-developing results in a pre-established standard database matched with identity information in the personalized mark areas to acquire the test results of the target components.

The acquired images can be corrected by various components of the data processing device; and a problem that the identification result is inaccurate because the images acquired by the mobile terminal have tremendous differences can be solved. The needed areas (the personalized mark areas and the result display areas) can be accurately segmented by a combined segmentation unit. Optionally, the color-developing results of the accurately segmented color-developing areas are read by a combined calculation unit.

Optionally, the data processing device is an implementation of a data processing device in the system for detecting the target components by utilizing the mobile terminal provided by the present disclosure. An optional implementation of the data processing center that can optionally perform data processing on the images shot by the mobile terminal to obtain reliable test results can be selected by those skilled in the art.

In one possible implementation manner, the data processing device is arranged on the mobile terminal; or the data processing device is arranged on a remote terminal in communication connection with the mobile terminal.

Compared with the technologies known by the inventors, the present disclosure has beneficial effects as follows:

(1) The present disclosure provides the method for detecting the target components by utilizing the mobile terminal. By utilizing the manner of arranging the test strips in the circumferential array, the needed test strip areas are segmented by identifying the location identifiers during image recognition to obtain the chroma values. The obtained chroma values are compared with the corresponding chroma values of the standard database to obtain the test results. Such a manner omits a process of directly identifying the color-developing area and decreases a disadvantage that an identification error in the width direction of the test strips is greater due to inaccurate edge identification. Meanwhile, multichannel detection can be realized in the processing procedures, and reliable detection results can be output during detection of the test strips in each channel.

(2) The present disclosure provides the method for the simultaneous determination of the multiple targets. The method only needs operations of conducting the chromatographic assay by the test strips, arranging the test strips, shooting the images by the mobile terminal and uploading the images to the system, and the test results can be obtained in time. The method that is simple in process, low in operating difficulty and easy to popularize, can realize accurate measurement for the target components in sample solutions, and can detect the test strips in multiple channels by utilizing the mobile terminal.

(3) The present disclosure further provides the system for detecting the target components by utilizing the mobile terminal. The target components can be detected by only using the detection device for sample solutions and the mobile terminal and the data processing device (may be cloud or mobile terminal) mounted with the image acquisition device and the test result receiving device. The device is easy to carry and can be used at home, convenient for market promotion and reliable in test result.

BRIEF DESCRIPTION OF THE DRAWINGS

To clearly describe technical solutions of embodiments of the present disclosure, drawings needing to be used in the embodiments will be briefly introduced below. It shall be understood that, the drawings below merely illustrate some embodiments of the present disclosure. Therefore, the drawings shall not be considered as a limitation to the scope. Other related drawings may be obtained by those ordinary skilled in the art in accordance with these drawings without making creative labor.

Figure 1:
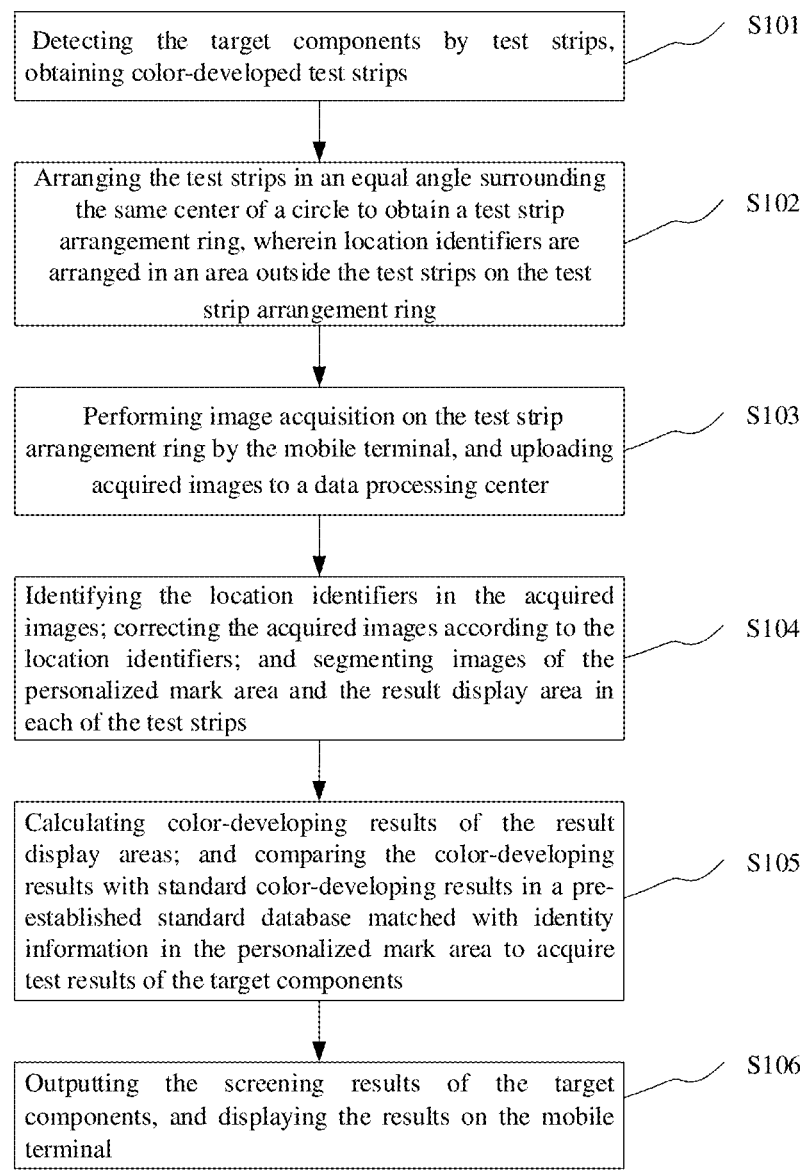
FIG. 1 is a flow chart of detecting target components by utilizing a mobile terminal provided by embodiments of the present disclosure.

Labels of drawings: test strip 100, detection disc 200, distinction tag block 300, contrast tag block 400, sample containing cavity 500, hollow cavity 510, bayonet 520, liquid dropping pipeline 530, clamping column 540, sample solution detection device 710, image acquisition device 720, data processing device 730, image correction unit 731, image segmentation unit 732, calculation unit 733 and test result receiving device 740

DETAILED DESCRIPTION OF THE INVENTION

For the purpose of making objects, technical solutions and advantages of the present disclosure more clear, clear and complete description will be made to the technical solutions of the present disclosure in conjunction with drawings in the embodiments of the present disclosure. Obviously, the described embodiments are merely a part of the embodiments of the present disclosure and not all the embodiments. Generally, components in the embodiments of the present disclosure that are described and illustrated in the drawings herein may be arranged and designed in various different configurations.

Therefore, the detailed description of the embodiments of the present disclosure provided in the drawings below is not intended to limit the protection scope of the present disclosure, but merely represents preferred embodiments of the present disclosure. Based on the embodiments in the present disclosure, all other embodiments obtained by those ordinary skilled in the art without making creative labor shall belong to the protection scope of the present disclosure.

It shall be noted that, similar symbols and letters represent similar terms in the drawings below. Therefore, once a certain term is defined in one drawing, the term shall not be further defined and explained in the followed drawings.

The present disclosure is realized by an immunological detection technology, so immunological detection is conducted by test strips in the method and system in the embodiments of the present disclosure.

A test strip in the embodiments of the present disclosure at least includes a sample pad used for dropping sample solutions. The sample pad is superposed with a colloidal gold pad in a staggered manner. A line MAX is set at the staggered part of the colloidal gold pad and the sample pad. A nitrocellulose membrane is overlapped at the other end of the colloidal gold pad. A water-absorbing material is overlapped at the other end of the nitrocellulose membrane. A T line (test line) and a C line (control line) are arranged on the nitrocellulose membrane and are used for carrying out a chromogenic reaction on targets in the sample solutions. In the test strip, the T line and C line will present different colors according to the content of the targets in the sample solutions. The content of the targets in the sample solutions is obtained by reading a color ratio of the T line and C line of the test strip. In the test strip, the sample pad and the colloidal gold pad may cover personalized marks to obtain a personalized mark area; and the water-absorbing material may also cover the personalized marks to obtain the personalized mark area, i.e., the area of the nitrocellulose membrane is a result display area.

The test strip in the embodiments of the present disclosure at least includes a personalized mark area, a result display area and a capillary area. The capillary area is used for adsorbing a liquid sample into the test strip and enabling the liquid sample to enter an area provided with a colloidal gold layer to carry out a chromogenic reaction; and the color-developed test result is shown in the result display area. The result display area of the test strip is generally provided with the T line (test line) and the C line (control line). The detection result may be obtained from the chromogenic reaction by virtue of a chromogenic reaction of the line T only; and the detection result may also be obtained by a combination of the color-developing results of the T line T and C line. The personalized mark area is used for setting the identity information, wherein the identity information includes but not limited to types, brands, production batch numbers and other information of the test strips. Meanwhile, the identifier information is identifiable information, such as QR codes and bar codes. In the embodiments of the present disclosure, the personalized mark area may be set in any area except for the result display area, as long as the result display area is not blocked.

A standard database shall be established for each type of test strips in advance before the target components are detected. A mapping relation is established between the chromogenic reaction results and the content of the target components in the standard database.

A typical but nonrestrictive mapping relation between the chromogenic reaction results and the content of the target components is an external standard method, i.e., chromatographic assay of the test strips with specific personalized marks is conducted by selecting existing sample solutions containing target components of known concentrations. Then, a corresponding relationship between the color-developing results of the test strips and the concentrations is detected by chromatography of the method provided by the present disclosure. Specifically, the existing sample solutions containing target components of known concentrations are detected by any operation of S101-S106, S301-S306 or S401-406, thereby obtaining the color-developing results matched with the concentrations of the target components.

How to detect the target components is described in detail below.

FIG. 1 is a flow chart of detecting target components by utilizing the mobile terminal provided by embodiments of the present disclosure. Referring to FIG. 1, a method for detecting the target components by utilizing the mobile terminal includes the following steps:

S101: Detecting the target components by test strips, obtaining color-developed test strips.

In one implementation, the operation of detecting the target components by the test strips may include an operation of detecting corresponding targets by utilizing different types of test strips. For example, urine samples are detected by test strips for urine; blood samples are detected by test strips for blood; the sample solutions may be the same, but multiple components in the sample solutions are screened, e.g., multiple pesticide residues, fungal toxins and environmental pollutants in the same tea sample solution are screened.

In another implementation, the operation of detecting the target components by the test strips may include an operation of detecting the same target in different samples by utilizing the same type of test strips. For example, tebuconazole (one kind of the pesticide residues) in different kinds of tea soup is detected.

Optionally, the types of the test strips in the present disclosure may include but not limited to test strips for testing pesticide residue components, various test strips used in the medical field and test strips for testing environmental pollution components.

S102: Arranging the test strips in an equal angle surrounding the same center of a circle to obtain a test strip arrangement ring, wherein location identifiers are arranged in an area outside the test strips on the test strip arrangement ring.

Figure 2:
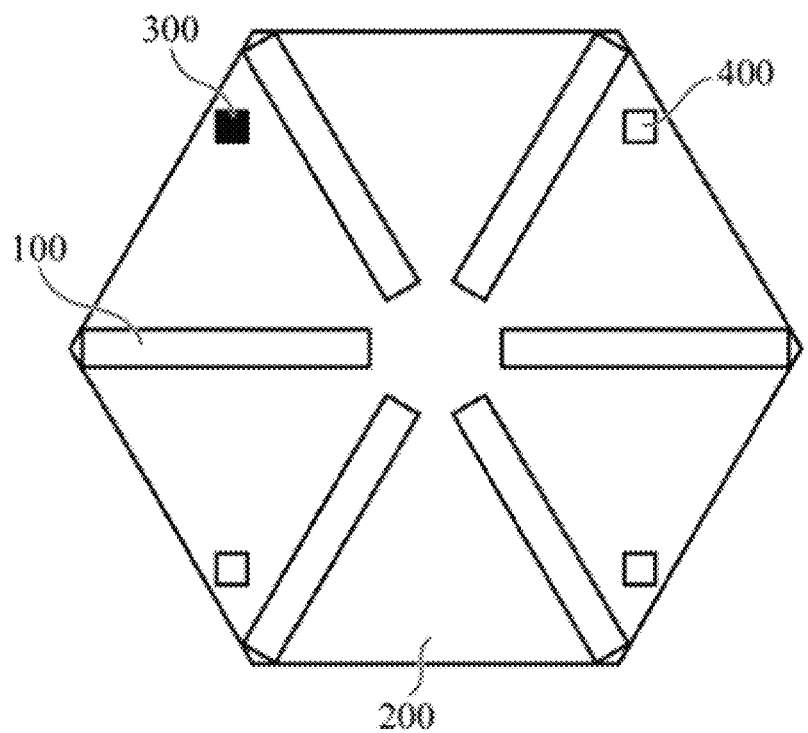
FIG. 2 is a structural schematic diagram of a detection disc and test strips arranged on the detection disc illustrated in one embodiment.

In one possible implementation, the test strip arrangement ring may be obtained by limiting the test strips on the detection disc. FIG. 2 is a structural schematic diagram of a detection disc and test strips arranged on the detection disc illustrated in one embodiment. Referring to FIG. 2, test strips 100 are arranged in an equal angle surrounding the center of a detection disc 200. As shown in FIG. 2, the detection disc 200 is a hexagonal detection disc; six test strips 100 are arranged in the hexagonal detection disc; one end of each of the test strips 100 is close to one angle of the detection disc 200; and each of the test strips extends towards the center of the detection disc 200, so that the other end of each of the test strips is close to the center of the detection disc. According to the length of the test strips 100 and the size of the detection disc 200, the end of each of the test strips close to the center of the detection disc is separated from the center of the detection disc, and the ends of the various test strips close to the center of the detection disc are separated from one another. Optionally, the above hexagonal detection disc and the arrangement manner of the test strips are illustrative only. The shape of the detection disc and the arrangement manner of the test strips are not specifically limited in the present disclosure. Other shapes of the detection disc and other arrangement manners of test strips may also be used.

An implementation of limiting the test strips on the detection disc may be as follows: test strip containing grooves used for containing the test strips are formed in the detection disc. When the test strips are limited in the test strip containing grooves, the upper surface of the test strips is optionally flush with the upper surface of the detection disc.

Optionally, that the test strips are limited by the test strip containing grooves is illustrative only. The test strips may also be limited by other limiting structures. For example, the test strips are limited by any one or a combination of at least two of cylindrical or multi-prismatic limiting blocks, limiting baffles and limiting slots. The limiting structures are not specifically limited in the present disclosure. All structures through which the test strips can be arranged into the test strip arrangement ring on the detection disc in the equal angle shall fall within the protection scope of the present disclosure.

In one possible implementation, the location identifiers may be tag blocks arranged on the detection disc 200. Referring to FIG. 2, the tag blocks may be distinction tag blocks 300 and contrast tag blocks 400 arranged on the detection disc 200. The distinction tag blocks 300 are used for being distinguished from the contrast tag blocks 400. In one possible implementation, shapes of the tag blocks may at least include vertexes and straight sides. Referring to FIG. 2, the shape of the tag blocks is square block. The upper surface of each of the tag blocks is square. Optionally, the shapes of the upper surfaces of the tag blocks may be other regular polygons or regular graphics with vertexes and straight sides. The shapes of the upper surfaces of the tag blocks in the present disclosure are not specifically limited, but preferably the regular graphics including the vertexes and straight sides, such as polygons or regular polygons and pentagrams.

In a specific implementation of the tag blocks, the upper surfaces of the distinction tag blocks 300 and contrast tag blocks 400 may have the same areas; and the distinction tag blocks 300 and contrast tag blocks 400 may be arranged in a circumferential array surrounding the center of the detection disc 200 together and close to the outer edge of the detection disc.

In a specific implementation of the tag blocks, the distinction tag blocks 300 and contrast tag blocks 400 are arranged on the outer edge of the detection disc, so that the tag blocks can be far away from the central position of the detection disc as much as possible. Thus, definition of the acquired image of each tag block is higher; and when the shot images are identified, the angles and positions of the images can be accurately corrected by the tag blocks.

In a specific implementation of the tag blocks, connecting lines of geometric centers of the distinction tag blocks 300 and contrast tag blocks 400 may be encircled into a square area; and the center of the square area coincides with the center of the detection disc. Such a design solution can simplify the correction algorithm and increase the information capacity and processing rate of the data processing center.

In a specific implementation of the tag blocks, the upper surface of the distinction tag blocks 300 is provided with a blue square, and the upper surface of the contrast tag blocks 400 is provided with three green squares; or the upper surface of the distinction tag blocks 300 is provided with a green square, and the upper surface of the contrast tag blocks 400 is provided with three blue squares.

In the above implementation process, blue and green are colors with relatively stable chroma, are slightly affected by brightness of the ambient light, are high in precision during boundary identification, and facilitate accurate correction of the acquired images.

Optionally, solutions of the shapes, colors and arrangement positions of the tag blocks shown in the above embodiments are illustrative only. The shapes, colors and arrangement positions of the tag blocks are not specifically limited in the present disclosure. All identification features through which to-be-detected images of test strips in the acquired images, particularly images of color-developing areas of the test strips can be corrected shall fall within the protection scope of the present disclosure. In another possible implementation, the location identifiers may be edges of the detection disc 200. In the detection disc 200 shown as FIG. 2, the location identifiers are six sides of the hexagonal detection disc. In another possible implementation, the location identifiers may be a combination of the tag blocks and the edges of the detection disc 200.

Optionally, shapes of the edges of the detection disc 200 are not specifically limited in the present disclosure. However, as a preferred implementation, the edges of the detection disc 200 are the regular graphics including the vertexes and straight sides.

S103: Performing image acquisition on the test strip arrangement ring by the mobile terminal, and uploading acquired images to a data processing center.

The mobile terminal in the embodiments of the present disclosure may include but not limited to a mobile phone, a laptop, a tablet personal computer and a POS machine, even includes an on-board computer and the like. All terminals equipped with image acquisition devices shall fall within the protection scope of the present disclosure.

In one possible implementation, pixels of image acquisition equipment of the mobile terminal are at least 8 million (such as 9 million, 10 million, 12 million, 15 million, 16 million, 18 million, 20 million, 23 million, 28 million, 35 million and 400 million).

The higher the pixels of the image acquisition equipment of the mobile terminal are, the higher the resolution of the acquired images is, the higher the identification accuracy of the images is, and the more accurate the detection results acquired according to the images are.

S104: Identifying the location identifiers in the acquired images; correcting the acquired images according to the location identifiers; and segmenting images of the personalized mark area and the result display area in each of the test strips.

In one possible implementation, the operation of correcting the acquired images according to the location identifiers after the location identifiers in the acquired images are identified includes determining positions of the personalized mark area and the result display area in each of the test strips in the corrected images according to a preset positional relationship between the location identifiers and the test strips. Optionally, the preset positional relationship between the location identifiers and the test strips may be a preset positional relationship, or a given positional relationship limited between the test strips and corresponding devices thereof. By taking the test strips limited on the detection disc as an example, a relationship between the positions for containing the test strips in the detection disc and the location identifiers on the detection disc is a fixed relationship. During image processing, the relationship between the location identifiers and the test strips is a given positional relationship between the test strips in the detection disc and the location identifiers, which because a positional relationship between the positions of the result display area and the personalized mark area in the test strips is also a given positional relationship in the test strips.

When the location identifiers are detection blocks on the detection disc, a method of correcting the acquired images includes determining the positions of the personalized mark area and the result display area in each of the test strips in the corrected images according to the preset positional relationship between the tag blocks and the test strips.

When the location identifiers are the edges of the detection disc, the method of correcting the acquired images includes: determining the positions of the personalized mark area and the result display area in each of the test strips in the corrected images according to a preset positional relationship between the edges of the detection disc and the test strips.

When the location identifiers are the detection block on the detection disc and the edges of the detection disc, the method of correcting the acquired images includes: determining the positions of the edges of the detection disc according to a preset positional relationship between the tag blocks and the edges of the detection disc; and determining the positions of the personalized mark area and the result display area in each of the test strips in the corrected images according to a preset positional relationship between the edges of the detection disc and the test strips.

The images are segmented after the positions of the personalized mark area and the result display area in each of the test strips are determined, so as to acquire the segmented images of the personalized mark area and the result display area in each of the test strips.

Optionally, the operation of determining the positions of the personalized mark area and the result display area according to the preset positional relationship is illustrative only. That the positions of the personalized mark area and the result display area are determined by an uncertain positional relationship is not specifically limited in the present disclosure.

S105: Calculating color-developing results of the result display areas; and comparing the color-developing results with standard color-developing results in a pre-established standard database matched with identity information in the personalized mark area to acquire test results of the target components.

In the embodiments of the present disclosure, the standard database is established for each type of the test strips in advance before detection. A mapping relation is formed between the color-developing results and the content of the target components in the standard database. In one possible implementation, the mapping relation between the color-developing results and the content of the target components is generally displayed by a T/C contrast curve in the display result. If the test strip is a line elimination type test strip, the mapping relation between the color-developing results and the content of the target components is generally displayed by an image chroma value of the T line.

After the color-developing results are obtained, concentration values of the targets corresponding to the color-developing results are found in the T/C contrast curve or a T-value alignment chart.

When a ratio result of the image chroma value of the T line and the image chroma value of the C line serves as the color-developing result, the image chroma value of the T line and the image chroma value of the C line shall be calculated. Optionally, the chroma value may include but not limited to an RGB value, a gray value or a photometric value.

In one possible implementation, when the color-developing result is calculated as the ratio of the image chroma value of the T line to the image chroma value of the C line, may include:

Making a ratio of an image chroma value of the T line relative to a background color to an image chroma value of the C line relative to the background color as the color-developing result. Optionally, a selection area of the background color may be located nearby the T line or the C line in the result display area. Since the color-developing result is mainly the ratio of the chroma of the T line and the C line, if the selected background color is too far away from the T line and the C line, inaccurate background noise is selected, thereby affecting reading accuracy of the color-developing result. When the background color is selected nearby the T line and the C line in the result display area, on the one hand, the result display area is made of the basically same material and has consistent light reflection behaviors; on the other hand, a background denoising effect is better due to the shorter distance.

Optionally, a selection area of the background color may be located between the T line and the C line. The T line and the C line share the same background color for denoising, thus the colorimetric result is more reliable.

In the above implementation process, that the image in a preset area between the T line and the C line serves as the background color has the advantage as follows: the ratio of the image chroma value of the T line to the image chroma value of the C line is more accurate. The reason is as follows: other interference colors may be subjected to chromatography by the test strips during detection, or the test strips are affected by the ambient light in the image shooting process. For the same test strip, the result display areas have the consistent background color during chromatography or under the same shooting condition. Taking the chroma value of the image in the preset area between the T line and the C line of the test strip in the acquired image as the background color is equivalent to filtering interference of the interference colors on the image chroma values of the T line and the C line. Thus it can be seen that, the calculation method is not affected by other interference colors, so that calculation of the color-developing result is more accurate.

S106: Outputting the screening results of the target components, and displaying the results on the mobile terminal.

After the chromatographic assay is conducted on the samples by the immunochromatographic test strips, a problem that the color-developing area is non-uniform in color developing often occurs. Therefore, accurately acquiring the color-developing result of the color-developing area becomes an important part of acquiring reliable detection results. However, in a manner of acquiring the color-developing result by virtue of the mobile terminal and the data processing, accurately segmenting the image in the color-developing area is a necessary condition for acquiring the accurate color-developing result. Relative to a combination of test strips in a non-circumferential array, each of the test strips arranged in the equal angle surrounding the same center of a circle may have the same distortion after the images are corrected; while in the combination of the test strips in the non-circumferential array, distortion differences still exist among different test strips after the images are corrected, thereby causing a problem that reading of the color-developing result is affected due to different sizes of the color-developing areas.

Based on the condition that each of the test strips has the same distortion in the corrected images, accurate positions of the personalized mark area and the result display area in the images of each of the test strips are obtained according to the preset positional relationship, so that a matching degree between the segmented result display areas and actual result display areas may be higher when the images of the test strips are segmented. Therefore, the reading accuracy of the color-developing result is increased; and accuracy of the detection result is further increased.

It can be seen that, the purpose of simultaneously detecting the multiple target components by utilizing the mobile terminal is achieved. The operating difficulty is low; operating equipment is convenient to carry; detection can be conducted at any time; and the detection results are reliable. Meanwhile, multichannel detection can be conducted; and multichannel detection results are all reliable.

Optionally, the test results of the target components may be output on a mobile terminal of the image acquisition equipment, may also be output on any mobile terminal that can perform data transmission with the data processing center, and may further be output on a data storage unit of the data processing center to store the data for call anytime.

Figure 3:
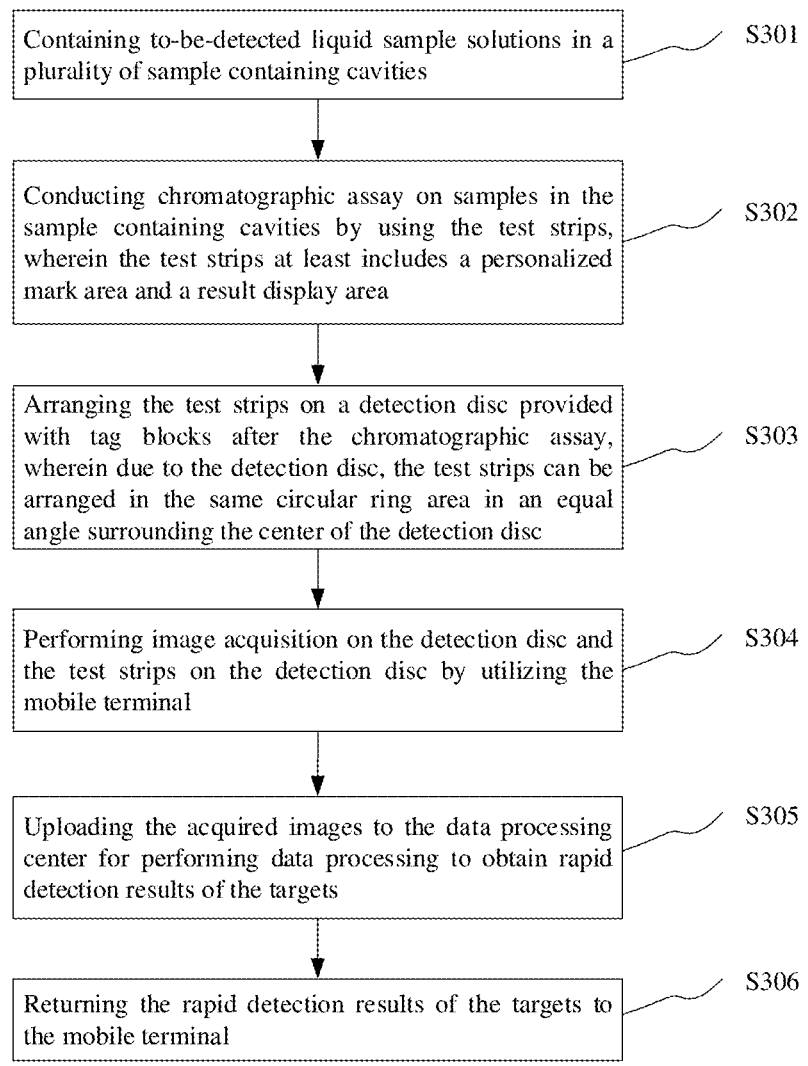
FIG. 3 is a flow chart of simultaneously detecting multiple targets provided by embodiments of the present disclosure.
Figure 5:
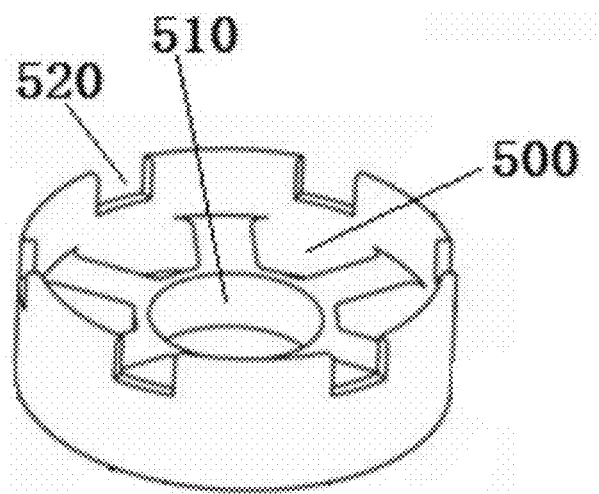
FIG. 5 is a structural schematic diagram of assembly of a plurality of sample containing cavities illustrated in one embodiment.

According to an implementation of the present disclosure, a method for simultaneously detecting multiple targets is further provided. FIG. 3 is a flow chart of simultaneously detecting multiple targets provided by the embodiments of the present disclosure. Referring to FIG. 3, the method for simultaneously detecting the multiple targets includes the following steps:

S301: Containing to-be-detected liquid sample solutions in a plurality of sample containing cavities. In one possible implementation, the plurality of sample containing cavities may be combined into a cylinder. FIG. 5 is a structural schematic diagram of assembly of the plurality of sample containing cavities illustrated in one embodiment. Referring to FIG. 5, the plurality of sample containing cavities 500 are integrally molded and encircled into a cylinder in the middle of which a hollow cavity 510 is formed; each of the sample containing cavities 500 includes an outer wall used for being encircled into an outer edge of the cylinder, and an inner wall used for being encircled into the middle cavity. In a preferred embodiment, a bayonet 520 used for clamping the test strips is formed in each of the outer walls. A width of the bayonet 520 is the same as or approximately the same as the width of the test strips, so that the test strip is just clamped in the bayonet 520, thereby avoiding sway of the test strip.

In one possible implementation, the width of the bottom of each of the sample containing cavities 500 or the whole sample containing cavities 500 (the width direction is perpendicular to a radius direction of the cylinder) is the same as or approximately the same as the width of the test strips.

In the above implementation process, when the test strips are inserted into the sample containing cavities 500 and limited by the width, the test strips are just clamped in the sample containing cavities 500. According to a combination of the above arrangement and the bayonet 520 on the outer wall, after the test strips are inserted into the sample containing cavities 500, two ends of the test strips are fixed, so that the test strips difficultly sway; and inclination angles of the test strips may be further well controlled.

In one possible implementation, the outer wall of each of the sample containing cavities 500 may be designed to be higher than the inner wall, i.e., the height of the outer wall of the hollow cavity 510 of the cylinder is smaller than that of the outer wall of the cylinder. During use of the sample containing cavities 500 of the above structure, only each of the sample containing cavities 500 is filled with liquid samples, and excessive liquid samples will overflow into the hollow cavity 510. Since each of the sample containing cavities 500 has the same volume, the liquid samples in the sample containing cavities 500 have the same volume. If the liquid samples contained in each of the sample containing cavities 500 do not overflow but only have preset heights, since the preset heights are limited by observation of users by naked eyes during dumping, the liquid samples in each of the sample containing cavities 500 difficultly have the same volume, thus the detection results are inaccurate.

S302: Conducting chromatographic assay on samples in the sample containing cavities by using the test strips, wherein the test strips at least includes a personalized mark area and a result display area. In one possible implementation, the sample solutions in the plurality of sample containing cavities have the same volume. Contact time of the test strips and the liquid samples in the sample containing cavities is the same. Inclination angles of the test strips inserted into the sample containing cavities are the same.

In the above implementation process, detection conditions of each of the test strips are basically the same during detection. The purpose is as follows: the detection results of each of the test strips are stable under almost the same detection condition, thereby avoiding inaccuracy of the detection results caused by different detection conditions.

S303: Arranging the test strips on a detection disc provided with tag blocks after the chromatographic assay, wherein due to the detection disc, the test strips can be arranged in the same circular ring area in an equal angle surrounding the center of the detection disc.

In one possible implementation, test strip containing grooves that are recessed downwards from the upper surface of the detection disc are formed in the detection disc, and are used for containing the test strips.

In one possible implementation, after the test strips are arranged on the detection disc, the upper surfaces of the test strips are flush with the upper surface of the detection disc.

In the above implementation process, when the upper surfaces of the test strips are flush with the upper surface of the detection disc, shadow produced by height differences between the test strips and the test strip containing grooves or caused by blocking of partial edges of the test strips by side walls of the test strip containing grooves during image acquisition can be decreased or avoided, thereby ensuring the accuracy of image acquisition.

In one possible implementation, isolation blocks used for separating the lower surfaces of the test strips from the bottoms of the test strip containing grooves are arranged at the bottoms of the test strip containing grooves.

In the above implementation process, the lower surfaces of the test strips may be separated from the bottoms of the test strip containing grooves by the isolation blocks, so that the test strip containing grooves are avoided from being contaminated by the test strips through which the sample solutions are subjected to chromatography. Therefore, the detection disc can be repeatedly used.

In one possible implementation, when the test strips are put into the test strip containing grooves, the personalized mark area is close to the center of a circle of the detection disc, and the border of an area containing the test strips in the test strip containing grooves is matched with the shape of the test strips.

In the above implementation process, when the personalized mark area is close to the center of a circle of the detection disc, the personalized mark area and the color-developing area can be shot in a narrower shooting range, and the acquired images are clearer. That the border of the area containing the test strips in the test strip containing grooves is matched with the shape of the test strips is to avoid forming shadow in the acquired images by the border of the area containing the test strips in the test strip containing grooves and the gaps among the edges of the test strips, so as not to further affect accurate reading of information in the personalized mark area.

S304: Performing image acquisition on the detection disc and the test strips on the detection disc by utilizing the mobile terminal.

S305: Uploading the acquired images to the data processing center for performing data processing to obtain rapid detection results of the targets.

S306: Returning the rapid detection results of the targets to the mobile terminal.

Optionally, the assembly of the sample containing cavities used in the method for simultaneously detecting the multiple targets is illustrative only.

Figure 4:
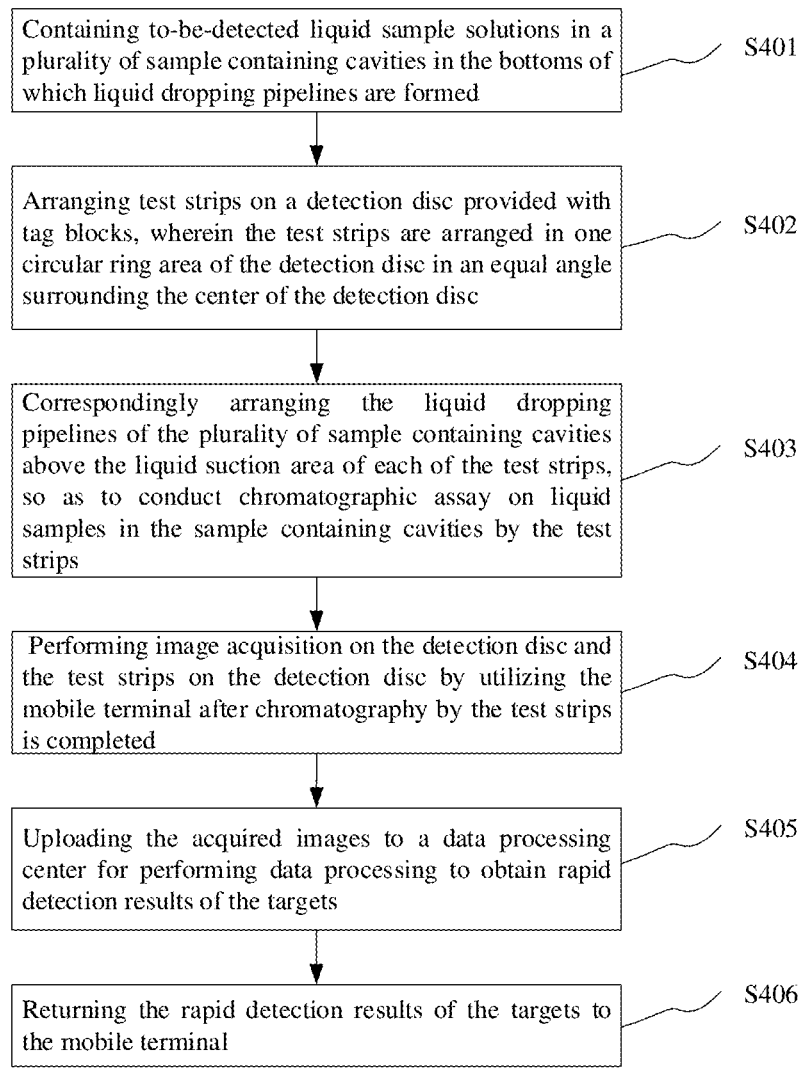
FIG. 4 is a flow chart of simultaneously detecting multiple targets provided by embodiments of the present disclosure.

According to another aspect of the present disclosure, a method for simultaneously detecting the multiple targets is further provided. FIG. 4 is a flow chart of simultaneously detecting the multiple targets provided by the embodiments of the present disclosure. Referring to FIG. 4, the method for simultaneously detecting the multiple targets includes the following steps:

S401: Containing to-be-detected liquid sample solutions in a plurality of sample containing cavities in the bottoms of which liquid dropping pipelines are formed.

Figure 6:
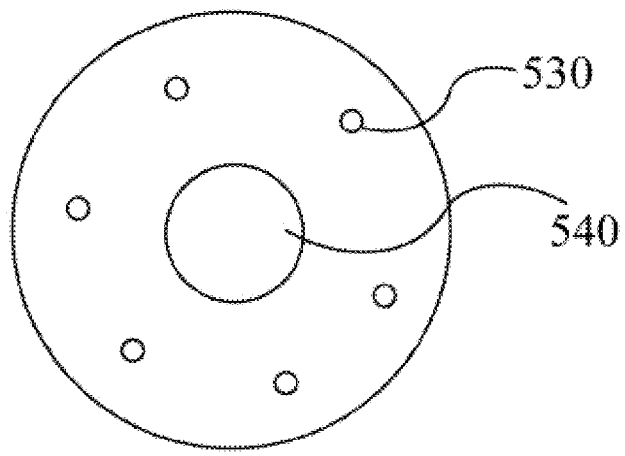
FIG. 6 is an upward view of an assembly structure of a plurality of sample containing cavities illustrated in one embodiment.

In one possible implementation, the plurality of sample containing cavities in the present embodiment are combined into a cylinder. The structure of the sample containing cavities is the same as the assembly of the plurality of sample containing cavities shown as FIG. 5. However, the differences from the structure shown as FIG. 5 are as follows: no bayonets are arranged on outer walls of the plurality of sample containing cavities in the embodiments of the present disclosure, but the liquid dropping pipelines are arranged at the bottoms; meanwhile, clamping columns 540 matched with the detection disc are further arranged. FIG. 6 is an upward view of an assembly structure of the plurality of sample containing cavities illustrated in one embodiment. Referring to FIG. 6, the liquid dropping pipeline 530 is arranged at the bottom of each of the sample containing cavities.

S402: Arranging test strips on a detection disc provided with tag blocks, wherein the test strips are arranged in one circular ring area of the detection disc in an equal angle surrounding the center of the detection disc; and each of the test strips at least includes a personalized mark area, a result display area and a liquid suction area.

In one possible implementation, test strip containing grooves that are recessed downwards from the upper surface of the detection disc are formed in the detection disc, and are used for containing the test strips.

In one possible implementation, after the test strips are arranged on the detection disc, the upper surfaces of the test strips are flush with the upper surface of the detection disc.

In the above implementation process, when the upper surfaces of the test strips are flush with the upper surface of the detection disc, shadow produced by height differences between the test strips and the test strip containing grooves or caused by blocking of partial edges of the test strips by side walls of the test strip containing grooves during image acquisition can be decreased or avoided, thereby ensuring the accuracy of image acquisition.

In one possible implementation, isolation blocks used for separating the lower surfaces of the test strips from the bottoms of the test strip containing grooves are arranged at the bottoms of the test strip containing grooves.

In the above implementation process, the lower surfaces of the test strips may be separated from the bottoms of the test strip containing grooves by the isolation blocks, so that the test strip containing grooves are avoided from being contaminated by the test strips through which the sample solutions are subjected to chromatography. Therefore, the detection disc can be repeatedly used.

In one possible implementation, when the test strips are put into the test strip containing grooves, the personalized mark area is close to the center of a circle of the detection disc, and the border of an area containing the test strips in the test strip containing grooves is matched with the shape of the test strips.

In the above implementation process, when the personalized mark area is close to the center of a circle of the detection disc, the personalized mark area and the color-developing area can be shot in a narrower shooting range, and the acquired images are clearer. That the border of the area containing the test strips in the test strip containing grooves is matched with the shape of the test strips is to avoid from forming shadow in the acquired images by the border of the area containing the test strips in the test strip containing grooves and the gaps among the edges of the test strips, so as not to further affect accurate reading of information in the personalized mark area.

S403: Correspondingly arranging the liquid dropping pipelines of the plurality of sample containing cavities above the liquid suction area of each of the test strips, so as to conduct the chromatographic assay on the liquid samples in the sample containing cavities by the test strips.

In one possible implementation, sample solution volumes in the plurality of sample containing cavities are the same; contact time of the test strips and the liquid samples is the same; and the positions of the liquid dropping pipelines arranged above the liquid suction area of the test strips are the same.

In the above implementation process, the detection conditions of the various test strips are basically the same during detection. The purpose is as follows: the detection result of each of the test strips is stable under almost the same detection condition, thereby avoiding inaccuracy of the detection results caused by different detection conditions.

S404: Performing image acquisition on the detection disc and the test strips on the detection disc by utilizing the mobile terminal after chromatography by the test strips is completed.

S405: Uploading the acquired images to a data processing center for performing data processing to obtain rapid detection results of the targets.

S406: Returning the rapid detection results of the targets to the mobile terminal.

Figure 7:
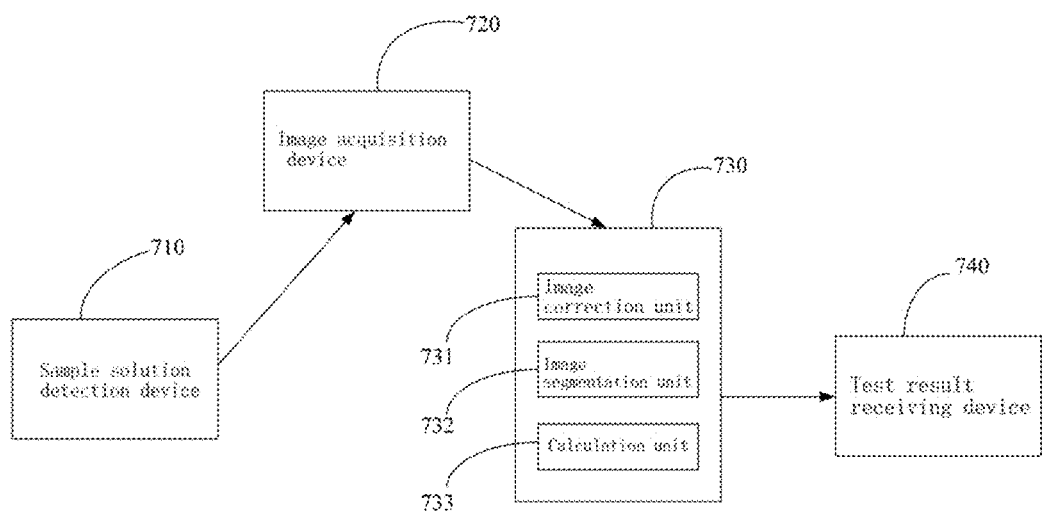
FIG. 7 is a structural schematic diagram of a system for detecting target components by utilizing a mobile terminal illustrated according to one embodiment.

According to another aspect of the present invention, a system for detecting the target components by utilizing the mobile terminal is further provided. FIG. 7 is a structural schematic diagram of the system for detecting the target components by utilizing the mobile terminal illustrated according to one embodiment. Referring to FIG. 7, the system for detecting the target components by utilizing the mobile terminal includes:

a sample solution detection device 710, including test strips and a detection disc, wherein each of the test strips at least includes a personalized mark area and a result display area; the detection disc is used for limiting the test strips to be arranged in an equal angle surrounding the same center of a circle to obtain a test strip arrangement ring; and location identifiers used for locating the test strips in the test strip arrangement ring are further arranged on the detection disc;

an image acquisition device 720, arranged on the mobile terminal and configured to perform image acquisition on the test strip arrangement ring;

a data processing device 730 configured to perform data processing on the acquired images and obtain test results of the target components; and a test result receiving device 740 configured to receive the test results of the target components and arranged on the mobile terminal.

The system for detecting the target components by utilizing the mobile terminal in the present embodiment is used for conducting the above method for detecting the target components by utilizing the mobile terminal; or the system is used for conducting the method for simultaneously detecting the multiple targets.

Optionally, the image acquisition device 720 and the test result receiving device 740 may be arranged on the mobile terminal.

In one possible implementation, the data processing device may include:

an image correction unit 731, configured to identify the location identifiers in the acquired images and correct the acquired images according to the location identifiers;

an image segmentation unit 732, configured to segment images of the personalized mark area and the result display area in each of the test strips; and a calculation unit 733, configured to calculate color-developing results of the result display areas, and compare the color-developing results with standard color-developing results in a pre-established standard database matched with identity information in the personalized mark areas to acquire the test results of the target components.

In the above implementation process, the correction method of the image correction unit refers to an image correction method in the method for detecting the target components by utilizing the mobile terminal. Unnecessary details are not given hereby.

In one possible implementation, the data processing device may be arranged on the mobile terminal. In another possible implementation, the data processing device may be arranged on a remote terminal in communication connection with the mobile terminal.

Effect Verification:

(1) Sample solutions of the pesticide tebuconazole are selected; the tebuconazole sample solutions of different concentrations are placed in sample containing cavities of the same volume; the chromatography is conducted by the test strips under the same detection condition; and color-developed test strips are obtained after the chromatography is completed;

(2) the color-developed test strips in the step (1) are arranged in the test strip containing grooves of the detection disc according to the operation specification requirements; images are shot by a mobile terminal (a mobile phone); and the shot images are uploaded to the data processing center to obtain a value T/C-mobile phone;

(3) the color-developed test strips in the step (1) are arranged in a handheld food safety analyzer GT-710 to obtain a value T/C-instrument.

Test results are shown as Table 1:

| Test strip No. | Test concentration-times of repetition | Value T/C-mobile phone | Mean Value | Value T/C-instrument | Mean Value |
|---|---|---|---|---|---|
| 1 | 20 ppb-2 | 0.779 | 0.714 | 0.356 | 0.361 |
| 2 | 20 ppb-1 | 0.648 |  | 0.365 |  |
| 3 | 10 ppb-2 | 0.842 | 0.850 | 0.569 | 0.589 |
| 4 | 10 ppb-1 | 0.857 |  | 0.609 |  |
| 5 | 0 ppb-2 | 1.396 | 1.257 | 1.078 | 1.117 |
| 6 | 0 ppb-1 | 1.117 |  | 1.156 |  |

The value T/C-mobile phone and the value T/C-instrument are subjected to linear fitting to obtain $R^2=0.9969$, i.e., trend variation of the two values is highly related.

It can be seen from the above test results that, the detection device for screening the targets in the present disclosure is shot by the mobile terminal (the mobile phone) to obtain the value T/C. The obtained value T/C is higher than the value T/C acquired by the instrument. However, it can be seen from linear fitting results of the two values that, the variation trend of the two values is highly consistent, i.e., when respectively independent standard curves are selected, determination of the test results of the targets is consistent.

The above descriptions are merely preferred embodiments of the present disclosure, rather than limiting the present disclosure. Various modifications and changes may be made to those skilled in the art. All modifications, equivalent replacements and improvements made in the spirit and principle of the present disclosure shall be included in the protection scope of the present disclosure.

INDUSTRIAL APPLICABILITY

According to the method for detecting the target components by utilizing the mobile terminal provided by the embodiments of the present disclosure, by utilizing the manner of arranging the test strips in the circumferential array, the location identifiers are identified in the image identification process; and the needed test strip areas are segmented to obtain the chroma values, so that the chroma values are compared with the chroma values in the corresponding standard database to obtain the test results. Such a manner omits the process of directly identifying the color-developing area and decreases a disadvantage that an identification error in the width direction of the test strips is greater due to inaccurate edge identification. Meanwhile, multichannel detection can be realized in the processing procedures, and reliable detection results can be output during detection of the test strips in each channel. In addition, such a manner is not affected by factors such as types of the mobile terminals and inclination of the shooting angles, and has the characteristics that requirements on professional degrees of operators are low and the targets can be qualitatively or quantitatively detected under conventional ambient light conditions anytime anywhere.

The method for simultaneously detecting the multiple targets provided by the embodiments of the present disclosure only needs operations of conducting the chromatographic assay by the test strips, arranging the test strips, shooting the images by the mobile terminal and uploading the images to the system, can obtain the test results, is simple in process, low in operating difficulty and easy to popularize, realizes accurate measurement during detection of the target components in the sample solutions, and can detect the test strips in multiple channels by utilizing the mobile terminal.

According to the system for detecting the target components by utilizing the mobile terminal provided by the embodiments of the present disclosure, the target components can be detected by using the sample solution detection device and the mobile terminal and the data processing device (may be cloud or mobile terminal) mounted with the image acquisition device and the test result receiving device only. The device is simple, small in size, easy to carry, simple in operation, convenient for market promotion and reliable in test results and can be used at home.

The invention claimed is:

1. A method for detecting target components by utilizing a mobile terminal, characterized by comprising:
    detecting to-be-detected sample solutions by test strips to obtain color-developed test strips, wherein the test strips at least comprises a personalized mark area and a result display area;
    arranging the test strips in an equal angle surrounding the same center of a circle to obtain a test strip arrangement ring;
    arranging location identifiers in a detection disc area outside the test strips on the test strip arrangement ring, wherein the location identifiers are tag blocks arranged on the detection disc, the tag blocks are distinction tag blocks and contrast tag blocks arranged on the detection disc, and the distinction tag blocks and the contrast tag blocks are arranged in a circumferential array surrounding the center of the detection disc together and close to the outer edge of the detection disc;
    performing image acquisition on the test strip arrangement ring by the mobile terminal;
    uploading acquired images to a data processing center;
    identifying the location identifiers in the acquired images;
    correcting the acquired images according to the location identifiers, wherein correcting the acquired images according to the location identifiers comprises: identifying positions and/or shapes of the location identifiers and correcting shooting angles of the acquired images and/or correcting position deviation of the acquired images according to the positions and/or shapes of the location identifiers;
    determining positions of the personalized mark area and the result display area in each of the test strips in the corrected images according to a preset positional relationship between the location identifiers and the test strips;
    segmenting images according to the determined positions of the personalized mark area and the result display area in each of the test strips to obtain the images of the personalized mark area and the result display area in each of the test strips;
    calculating color-developing results of the result display areas;
    comparing the color-developing results with standard color-developing results in a pre-established standard database matched with identity information in the personalized mark areas;
    acquiring test results of the target components;
    outputting the test results of the target components; and
    displaying the test results on the mobile terminal.

2. The method according to claim 1, characterized in that the location identifiers have preset shapes and are arranged at preset positions;
    and the shapes of the location identifiers are shapes that have obvious vertexes and straight sides.

3. The method according to claim 1, characterized in that the test strip arrangement ring is obtained by limiting the test strips on a detection disc.

4. The method according to claim 1, characterized in that segmenting the images of the personalized mark area and the result display area in each of the test strips comprises:
    identifying the tag blocks in the acquired images; correcting the acquired images according to the tag blocks; determining positions of the personalized mark area and the result display area in each of the test strips in the corrected images according to a preset positional relationship between the tag blocks and the test strips; and segmenting the images according to the determined positions of the personalized mark area and the result display area in each of the test strips to obtain segmented images of the personalized mark area and the result display area in each of the test strips;
    segmenting the images of the personalized mark area and the result display area in each of the test strips comprises:
    identifying the tag blocks and the edges of the detection discs in the acquired images; correcting the acquired images according to the tag blocks and the edges of detection discs; determining positions of the personalized mark area and the result display area in each of the test strips in the corrected images according to common information of the tag blocks and the edges of detection discs and a preset positional relationship between the common information and the test strips; and segmenting the images according to the determined positions of the personalized mark area and the result display area in each of the test strips to obtain segmented images of the personalized mark area and the result display area in each of the test strips.

5. The method according to claim 1, characterized in that the result display area in each test strip comprises a T line and a C line;
    the color-developing result is a ratio of an image chroma value of the T line to an image chroma value of the C line; or the color-developing result is an image chroma value of the T line; and the chroma value comprises an RGB value, a gray value or a photometric value.

6. The method according to claim 5, characterized in that calculating the color-developing result as the ratio of the image chroma value of the T line to the image chroma value of the C line comprises:
taking a ratio of the image chroma value of the T line relative to a background color to the image chroma value of the C line relative to the background color as the color-developing result.

7. The method according to claim 6, characterized in a selection area of the background color is located nearby the T line or the C line in the result display area; or the selection area of the background color is located between the T line and the C line.

8. The method according to claim 1, characterized in that detecting the target components by the test strips comprises:
respectively arranging the test strips in a plurality of sample containing cavities for containing the target components, wherein sample solution volumes in the plurality of sample containing cavities are the same; and the test strips arranged in the sample containing cavities have the same angle of inclination and the same arrangement time.

9. The method according to claim 1, characterized in that the method further comprises: calibrating orders of the test strips in the test strip arrangement ring by the tag blocks.

10. The method according to claim 1, characterized in that pixels of image acquisition equipment of the mobile terminal are at least 8 million.

11. The method according to claim 1, characterized in that after the test strips are arranged on the detection disc, the upper surface of the test strips is flush with the upper surface of the detection disc;
and the upper surface of the result display area is flush with the upper surface of the detection disc.

12. The method according to claim 1, characterized in the test strips in the test strip arrangement ring are sorted in sequence clockwise or anticlockwise by taking one tag block that can be distinguished from the rest tag blocks as a starting point of the order.

13. A method for simultaneously detecting multiple targets, characterized by comprising:
containing to-be-detected liquid sample solutions in a plurality of sample containing cavities in the bottoms of which liquid dropping pipelines are formed;
arranging test strips on a detection disc provided with location identifiers, wherein the test strips are arranged in one circular ring area of the detection disc in an equal angle surrounding the center of the detection disc, the location identifiers are tag blocks arranged on the detection disc, the tag blocks are distinction tag blocks and contrast tag blocks arranged on the detection disc, and the distinction tag blocks and the contrast tag blocks are arranged in a circumferential array surrounding the center of the detection disc together and close to the outer edge of the detection disc, and each of the test strips at least comprises a personalized mark area, a result display area and a liquid suction area;
correspondingly arranging the liquid dropping pipelines of the plurality of sample containing cavities above the liquid suction area of each of the test strips, so as to conduct the chromatographic assay on liquid samples in the sample containing cavities by the test strips;
performing image acquisition on the detection disc and the test strips on the detection disc by utilizing the mobile terminal after chromatography of the test strips is completed;
uploading the acquired images to a data processing center for performing data processing;
identifying the location identifiers in the acquired images;
correcting the acquired images according to the location identifiers, wherein correcting the acquired images according to the location identifiers comprises: identifying positions and/or shapes of the location identifiers and correcting shooting angles of the acquired images and/or correcting position deviation of the acquired images according to the positions and/or shapes of the location identifiers;
determining positions of the personalized mark area and the result display area in each of the test strips in the corrected images according to a preset positional relationship between the location identifiers and the test strips;
segmenting images according to the determined positions of the personalized mark area and the result display area in each of the test strips to obtain segmented images of the personalized mark area and the result display area in each of the test strips;
acquiring detection results of the targets; and
returning the detection results of the targets to the mobile terminal,
wherein after the test strips are arranged on the detection disc, the upper surface of the test strips is flush with the upper surface of the detection disc, and the upper surface of the result display area is flush with the upper surface of the detection disc.

14. The method according to claim 13, characterized in that the location identifiers arranged on the upper surface of the detection disc are tag blocks, used for locating and tagging the test strips in the image acquisition and processing procedures.

15. The method according to claim 14, characterized in the tag blocks comprise distinction tag blocks and contrast tag blocks; and the distinction tag blocks are used for being distinguished from the contrast tag blocks; and the total number of the distinction tag blocks and contrast tag blocks is not less than three.

16. The method according to claim 14, characterized in shapes of the tag blocks at least comprise vertexes and straight sides; or the tag blocks comprise one blue square color block and three green square color blocks, or the tag blocks comprise one green square color block and three blue square color blocks.

17. The method according to claim 13, characterized in that the upper surface of the detection disc is a regular polygon.

18. The method according to claim 17, characterized in the upper surface of the detection disc is a diffuse reflection surface.

19. The method according to claim 13, characterized in that when the chromatographic assay is conducted on the samples in the sample containing cavities by the test strips, the sample solutions in the plurality of sample containing cavities have the same quantity; and contact time of the test strips and the liquid samples in the sample containing cavities is the same.

20. The method according to claim 19, characterized in that when the test strips are located at the bottoms of the sample containing cavities, the positions of the liquid dropping pipelines arranged above the liquid suction area of the test strips are the same.

21. The method according to claim 13, characterized in that pixels of image acquisition equipment of the mobile terminal are at least 8 million.

22. The method according to claim 13, characterized in that test strip containing grooves that are recessed downwards from the upper surface of the detection disc are formed in the detection disc, and are used for containing the test strips.

23. The method according to claim 22, characterized in isolation blocks used for separating the lower surfaces of the test strips from the bottoms of the test strip containing grooves are arranged at the bottoms of the test strip containing grooves; or
the test strips are put into the test strip containing grooves, the personalized mark area is close to the center of circle of the detection disc, and the border of an area containing the test strips in the test strip containing grooves is matched with the shape of the test strips.

24. A system for detecting target components by utilizing a mobile terminal, characterized by comprising:
a sample solution detection device, comprising test strips and a detection disc, wherein each of the test strips at least comprises a personalized mark area and a result display area; the detection disc is used for defining the test strips to be arranged in an equal angle surrounding the same center of circle to obtain a test strip arrangement ring; and location identifiers used for locating the test strips in the test strip arrangement ring after image acquisition are arranged on the detection disc; the location identifiers are tag blocks arranged on the detection disc, the tag blocks are distinction tag blocks and contrast tag blocks arranged on the detection disc, and the distinction tag blocks and the contrast tag blocks are arranged in a circumferential array surrounding the center of the detection disc together and close to the outer edge of the detection disc;
an image acquisition device, arranged on the mobile terminal, and configured to perform image acquisition on the test strip arrangement ring;
a data processing device, configured to:
perform data processing on the acquired images,
identify the location identifiers in the acquired images,
correct the acquired images according to the location identifiers, wherein correcting the acquired images according to the location identifiers comprises: identifying positions and/or shapes of the location identifiers and correcting shooting angles of the acquired images and/or correcting position deviation of the acquired images according to the positions and/or shapes of the location identifiers,
determine positions of the personalized mark area and the result display area in each of the test strips in the corrected images according to a preset positional relationship between the location identifiers and the test strips,
segment images according to the determined positions of the personalized mark area and the result display area in each of the test strips to obtain the segmented images of the personalized mark area and the result display area in each of the test strips, and
obtain test results of the target components; and
a test result receiving device, configured to receive the test results of the target components and arranged on the mobile terminal.

25. The system according to claim 24, characterized in that the system is used for conducting:
a method for simultaneously detecting multiple targets, characterized by comprising:
containing to-be-detected liquid sample solutions in a plurality of sample containing cavities in the bottoms of which liquid dropping pipelines are formed;
arranging test strips on a detection disc provided with location identifiers, wherein the test strips are arranged in one circular ring area of the detection disc in an equal angle surrounding the center of the detection disc; and each of the test strips at least comprises a personalized mark area, a result display area and a liquid suction area;
correspondingly arranging the liquid dropping pipelines of the plurality of sample containing cavities above the liquid suction area of each of the test strips, so as to conduct the chromatographic assay on liquid samples in the sample containing cavities by the test strips;
performing image acquisition on the detection disc and the test strips on the detection disc by utilizing the mobile terminal after chromatography of the test strips is completed;
uploading the acquired images to a data processing center for performing data processing; identifying the location identifiers in the acquired images;
correcting the acquired images according to the location identifiers;
determining positions of the personalized mark area and the result display area in each of the test strips in the corrected images according to a preset positional relationship between the location identifiers and the test strips;
segmenting images according to the determined positions of the personalized mark area and the result display area in each of the test strips to obtain segmented images of the personalized mark area and the result display area in each of the test strips;
acquiring detection results of the targets; and
returning the detection results of the targets to the mobile terminal.

26. The system according to claim 24, characterized in that:
i) the data processing device comprises:
an image correction unit, configured to identify the location identifiers in the acquired images and correct the acquired images according to the location identifiers;
an image segmentation unit, configured to segment images of the personalized mark area and the result display area in each of the test strips; and
a calculation unit, configured to calculate color-developing results of the result display areas, and compare the color-developing results with standard color-developing results in a pre-established standard database matched with identity information in the personalized mark areas to acquire the test results of the target components; and/or
ii) the data processing device is arranged on the mobile terminal; or the data processing device is arranged on a remote terminal in communication connection with the mobile terminal.

27. A method for simultaneously detecting multiple targets, characterized by comprising:
containing to-be-detected liquid sample solutions in a plurality of sample containing cavities;
conducting the chromatographic assay on the samples in the sample containing cavities by test strips, wherein each of the test strips at least comprises a personalized mark area and a result display area;
arranging the test strips on a detection disc provided with location identifiers after the chromatographic assay, wherein due to the detection disc, the test strips can be arranged in the same circular ring area in an equal angle surrounding the center of the detection disc, the location identifiers are tag blocks arranged on the detection disc, and the tag blocks are distinction tag blocks and contrast tag blocks arranged on the detection disc, and the distinction tag blocks and the contrast tag blocks are arranged in a circumferential array surrounding the center of the detection disc together and close to the outer edge of the detection disc;

performing image acquisition on the detection disc by utilizing the mobile terminal;

uploading the acquired images to a data processing center for performing data processing;

identifying the location identifiers in the acquired images;

correcting the acquired images according to the location identifiers, wherein correcting the acquired images according to the location identifiers comprises: identifying positions and/or shapes of the location identifiers and correcting shooting angles of the acquired images and/or correcting position deviation of the acquired images according to the positions and/or shapes of the location identifiers;

determining positions of the personalized mark area and the result display area in each of the test strips in the corrected images according to a preset positional relationship between the location identifiers and the test strips;

segmenting images according to the determined positions of the personalized mark area and the result display area in each of the test strips to obtain segmented images of the personalized mark area and the result display area in each of the test strips;

acquiring detection results of the targets; and returning the detection results of the targets to the mobile terminal.

28. The method according to claim 27, characterized in that when the chromatographic assay is conducted on the samples in the sample containing cavities by the test strips, the sample solutions in the plurality of sample containing cavities have the same quantity; and contact time of the test strips and the liquid samples in the sample containing cavities is the same; when the test strips are inserted into the sample containing cavities, the inclination angle of the test strips inserted into the sample containing cavities is the same.

* * * * *